United States Patent
Aboul-Hosn et al.

(10) Patent No.: US 6,210,133 B1
(45) Date of Patent: Apr. 3, 2001

(54) BLOOD PUMP WITH STERILE MOTOR HOUSING

(75) Inventors: Walid Najib Aboul-Hosn, Sacramento; Sedig Noor, Stockton; William Russell Kanz; Michael Guidera, both of Sacramento, all of CA (US); Robert G. Matheny, Carmel, IN (US); Kelly J. McCrystle, Healdsburg, CA (US)

(73) Assignee: A-Med Systems, Inc., West Sacramento, CA (US)

( * ) Notice: Subject to any disclaimer, the term of this patent is extended or adjusted under 35 U.S.C. 154(b) by 0 days.

(21) Appl. No.: 09/166,135

(22) Filed: Sep. 30, 1998

(51) Int. Cl.⁷ .................................................. F04B 35/04
(52) U.S. Cl. ........................................ 417/423.1; 604/151
(58) Field of Search ................................ 417/423.1, 420, 417/360, 423.14; 600/16, 17; 623/3; 604/131, 151, 50

(56) References Cited

U.S. PATENT DOCUMENTS

| | | | |
|---|---|---|---|
| 3,048,116 | * 8/1962 | Konrad | .................................. 417/360 |
| 4,135,253 | 1/1979 | Reich et al. . | |
| 4,515,592 | 5/1985 | Frankhouser . | |
| 4,625,712 | 12/1986 | Wampler . | |
| 4,846,154 | 7/1989 | Wampler et al. . | |
| 4,895,557 | 1/1990 | Moise et al. . | |
| 4,898,518 | 2/1990 | Hubbard et al. . | |
| 4,984,972 | 1/1991 | Clausen et al. . | |
| 5,118,264 | * 6/1992 | Smith | ............................. 417/423.11 |
| 5,145,333 | * 9/1992 | Smith | .................................... 415/900 |
| 5,147,186 | 9/1992 | Buckholtz . | |
| 5,393,207 | * 2/1995 | Maher et al. | ...................... 417/423.7 |
| 5,539,503 | 7/1996 | Johnson . | |
| 5,580,216 | 12/1996 | Munch . | |
| 5,741,234 | 4/1998 | Aboul-Hosn . | |
| 5,746,709 | 5/1998 | Rom et al. . | |
| 5,785,013 | * 7/1998 | Sinn et al. | ....................... 417/423.14 |

FOREIGN PATENT DOCUMENTS

378906 * 8/1923 (DE) .................................... 415/913
WO94/17304 * 8/1994 (WO) .

OTHER PUBLICATIONS

Brochure for Patented Cath–Gard® shield.
Brochure for 3M™ Sarns™ Centrifugal System.
Brochure for 3M™ Sarns and CDI Health Care Cardiovascular System Products.

* cited by examiner

Primary Examiner—Charles G. Freay
(74) Attorney, Agent, or Firm—Jonathan Spangler

(57) ABSTRACT

A blood pump for use in CPB and other heart surgeries includes a reusable motor stator element which is enclosed in a disposable, sterile pump housing. The reusable, non-sterilized motor stator element is completely encased by the pump housing so that the motor stator can be reused without sterilization. The sterile housing allows the blood pump to be placed closed to the patient and within the sterile surgical field. The placement of the blood pump close to the heart during heart surgery greatly reduces the priming volume of the system thereby reducing the amount of saline or drugs which are introduced the patient's blood. The sterile housing may be evacuated to reduce the risk of emboli which may occur due to the failure of a seal.

20 Claims, 6 Drawing Sheets

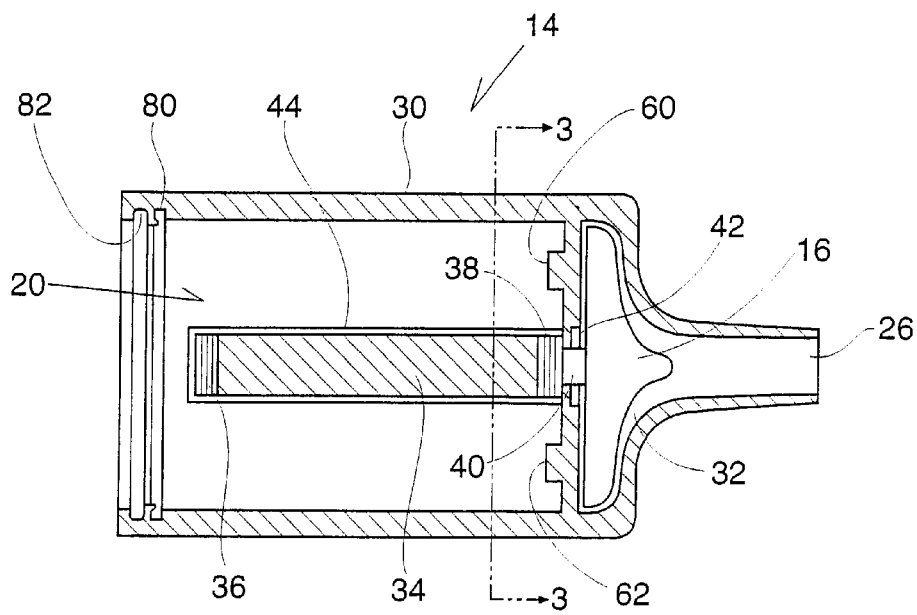
Fig. 2
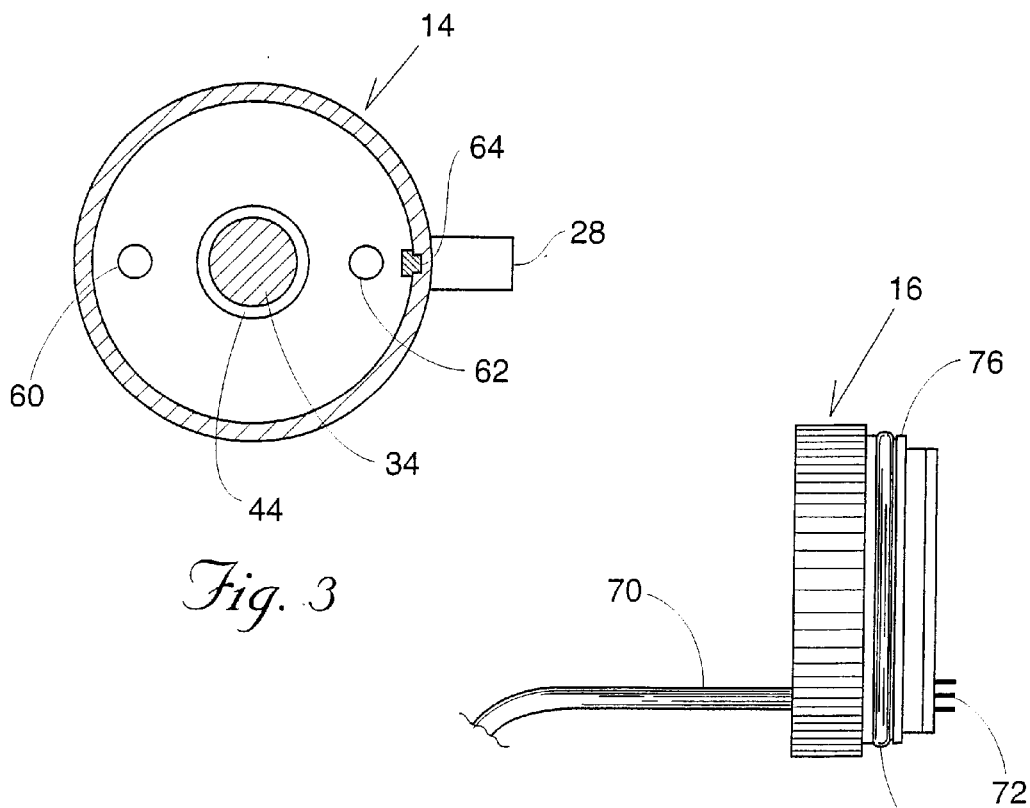
Fig. 3
Fig. 4

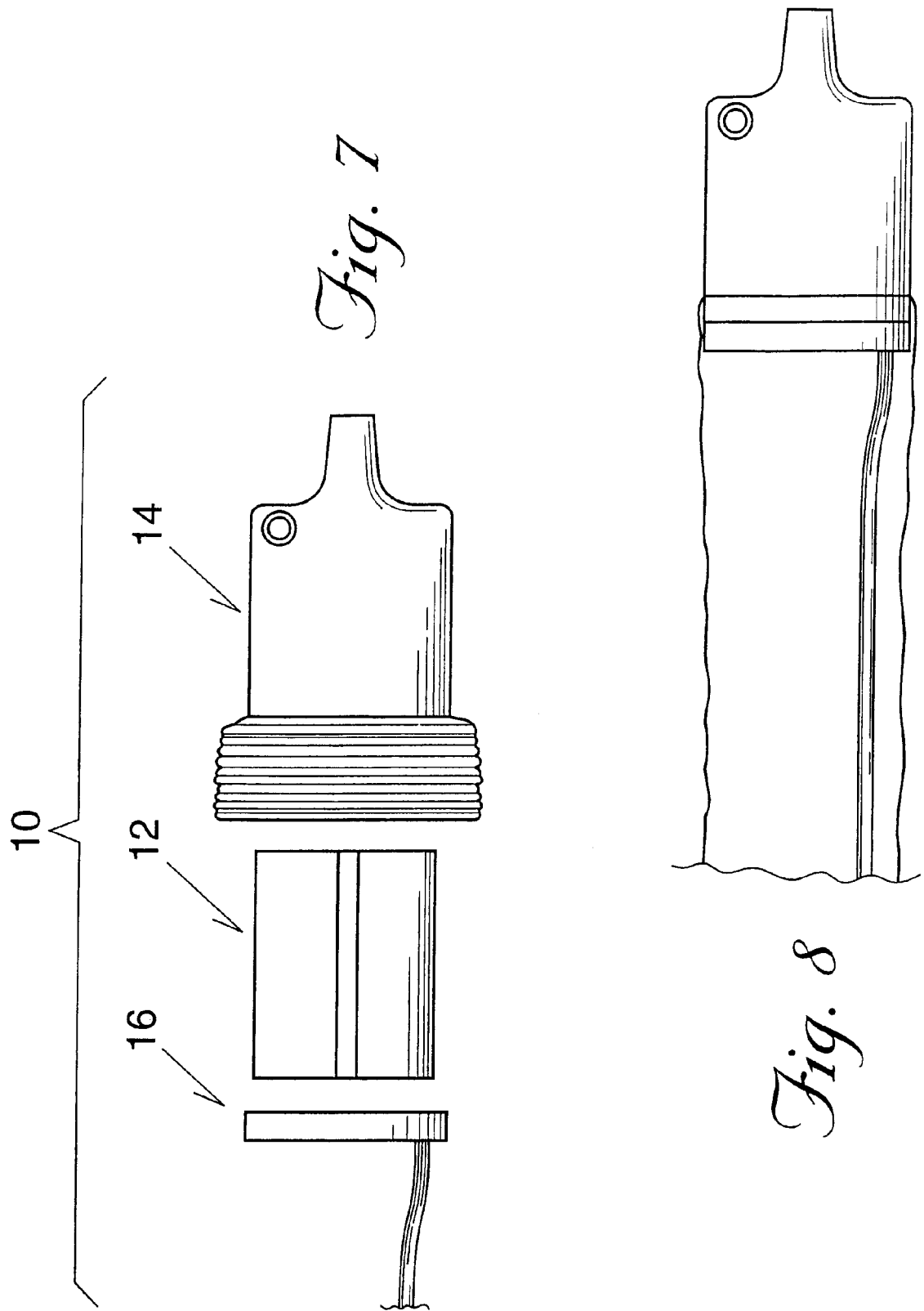

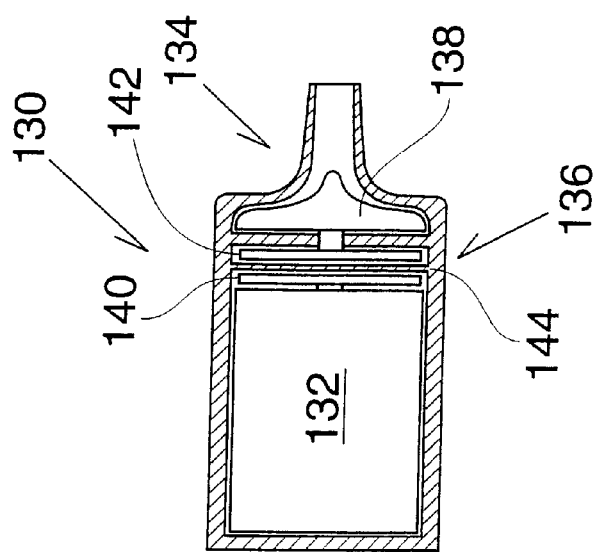
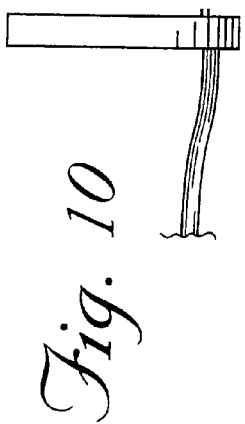
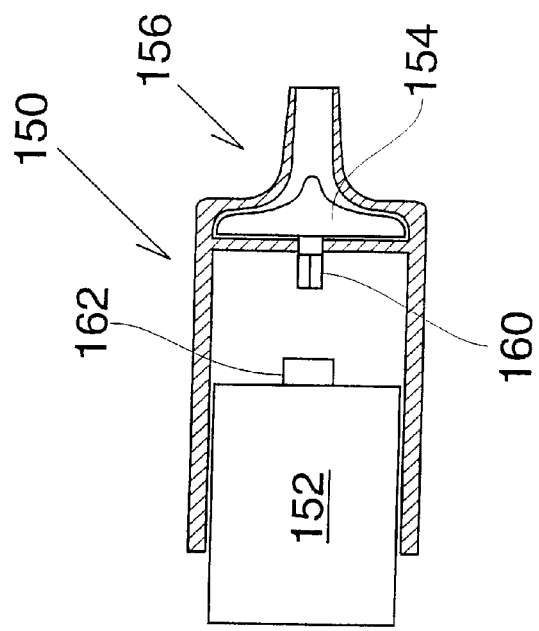

BLOOD PUMP WITH STERILE MOTOR HOUSING

BACKGROUND OF THE INVENTION

1. Field of the Invention

The invention relates to a blood pump, and more particularly, the invention relates to a centrifugal blood pump with a disposable pump element and a reusable motor element.

2. Brief Description of the Related Art

Blood pumps used in surgical procedures such as cardiopulmonary bypass (CPB) and coronary artery bypass grafting (CABG) are single-use devices. These blood pumps are generally powered by a reusable motor which drives the pump through a magnetic coupling. However, the reusable motors are not sterilizable. Thus, the motor and attached pump are positioned outside the sterile surgical field at a location away from the patient. The disposable pump which is driven by the motor is connected to the patient by long lengths of tubing which transport the patient's blood to and from the blood pump. The long lengths of tubing increase the priming volume of the pump which is the amount of the patient's blood and/or saline which must be drawn into the tubing and the pump to prime the pump before blood begins to be returned to the patient.

Long lengths of tubing connecting the pump to the patient also increase the amount of foreign material which comes into contact with the patient's blood, increasing trauma to the patient. A typical CPB circuit includes several feet of flexible tubing that the patient's blood flows through. In order to prevent blood clots, the patient's blood is generally treated with Heparin. The use of Heparin is preferably minimized because Heparin prevents the blood from clotting.

In addition to the priming volume problem with known blood pumps the magnetic coupling for transmitting rotation between the pump and the motor has associated disadvantages. With the magnetic coupling, accurate measurements of the load on the pump are difficult to obtain because of the possible slippage that occurs between the magnets of the magnetic coupling. Because the coupling is not direct, the magnetic plates may slip relative to each other resulting in the motor turning faster than the pump impeller. Further, the current drawn by the motor to control the rotation of the rotor, is used in these devices for measurement of impeller loads. Due to the possible slippage of the magnetic coupling between the pump impeller and motor unit an accurate measurement of current is difficult to obtain.

Previous attempts to move the blood pump closer to the patient have involved the use of a cable drive between the motor and the pump which allows the sterile pump to be located within the sterile surgical field while the motor is placed outside of the sterile surgical field. The use of a cable drive increases the load on the motor due to friction between the cable housing and the cable and makes it more difficult to accurately control the pumping volume due to rpm fluctuations. Also, the use of a cable introduces the possibility of the cable breaking or becoming kinked during the surgical procedure causing pump failure.

Blood pumps may be used during still heart surgery where the bypass pump is needed to perform the work of the heart. Alternatively, heart surgery may be done on a beating heart. During beating heart surgery the blood pump is used to provide supplemental support. In addition, during a beating heart surgical procedure the heart may fibrillate and cease pumping blood thereby requiring full support. Therefore it is necessary that the blood pump utilized for beating heart supplemental support be capable of providing full CPB support if needed. In either stopped heart or beating heart surgery, it is desirable to minimize the priming volume of the blood pump by placing the pump as close as possible to the surgical site. By placing the pump closer to the surgical field, the amount of saline required to prime the bypass circuit is reduced which reduces the likelihood that a transfusion will be required.

Accordingly, it would be desirable to provide a blood pump which can be positioned within the surgical field close to the surgical site to minimize the priming volume of the pump. In order to position the pump within the surgical field close to the heart, the pump and associated motor must be provided in a sterile condition.

SUMMARY OF THE INVENTION

The present invention relates to a blood pump including a reusable motor stator element having a substantially cylindrical central cavity and an electrical connection, a disposable pump element having an impeller connected to a substantially cylindrical magnetic rotor which is configured to fit within the substantially cylindrical central cavity of the motor stator element, and a cap member having a fluid tight connection for connecting the cap member to the pump element to completely enclose and isolate the motor stator element within a pump housing formed by the pump element and the cap member.

In accordance with another aspect of the present invention, a sterile blood pump assembly includes a blood pump element having a blood inlet, a blood outlet, and an impeller for pumping blood from the inlet to the outlet. The impeller is connected to a magnetic rotor element. A motor stator element is configured to be received on the blood pump with the magnetic rotor element of the blood pump received within a coil winding of the motor stator element. The motor stator element rotates the magnetic rotor element and the impeller of the blood pump element. A sterile housing surrounds the motor stator element and isolates the motor stator element from a surrounding environment. Further, the sterile housing surrounding the motor stator may be evacuated creating a vacuum such that if the seals in the blood pump fail, fluid is drawn into the chamber eliminating the possibility of emboli forming within the patient's blood stream.

In accordance with an additional aspect of the present invention, a method of pumping blood during heart surgery includes the steps of isolating a non-sterile motor element within a sterile pump housing, the sterile pump housing including an impeller connected to a rotor which is rotated by activation of a stator element of the non-sterile motor element, placing the pump housing within a sterile surgical field, and pumping a patient's blood with the sterile blood pump by rotation of the impeller.

The present invention provides advantages of a compact blood pump and motor assembly which can be placed within the sterile field close to the surgical incision or even within the chest cavity.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 2 is a side cross sectional view of a pump element with the motor removed;

FIG. 3 is a cross sectional end view of the pump element taken along line 3—3 of FIG. 2;

FIG. 4 is a side view of a cap for the sterile motor housing;

FIG. 7 is an exploded side view of a blood pump with a flexible sleeve;

FIG. 8 is an assembled side view of the blood pump with the flexible sleeve of FIG. 7 illustrating the flexible sleeve in an expanded condition;

FIG. 9 is a side cross sectional view of an alternative embodiment of a blood pump with a magnetic motor coupling; and FIG. 10 is a side cross sectional view of an alternative embodiment of a blood pump with a mechanical motor coupling.

DETAILED DESCRIPTION OF THE PREFERRED EMBODIMENTS

Figure 1:
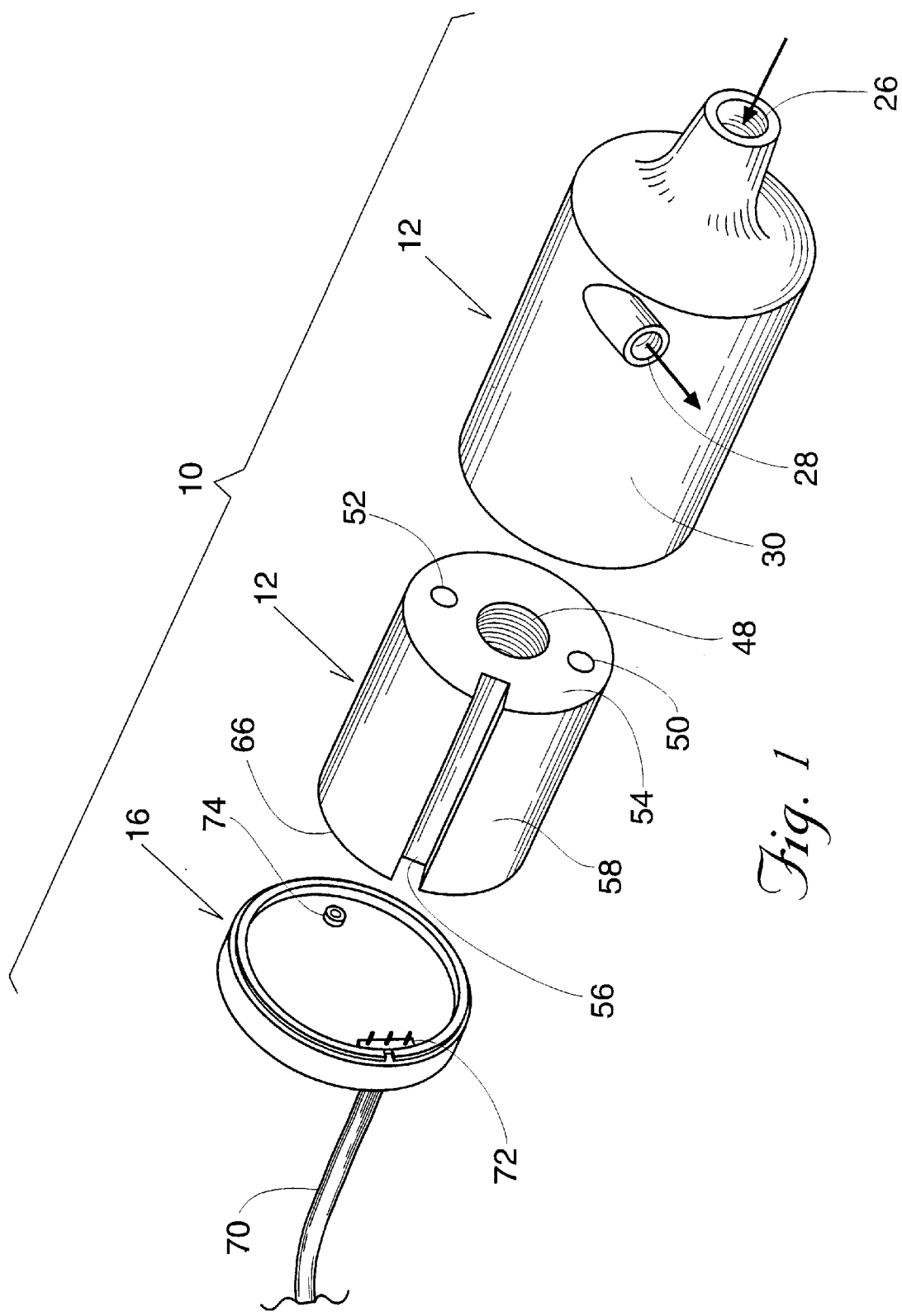
FIG. 1 is an exploded perspective view of a blood pump according to the present invention.

A blood pump 10 having a reusable motor stator element 12, a pump body 14, and a cap 16, is illustrated in FIG. 1. The entire blood pump 10 is sufficiently small that it may be placed within the surgical field during CPB and other heart surgery. The pump body 14 and cap 16 together provide a sterile casing for the reusable motor stator element 12. The motor stator element 12 when completely encased by the body 14 and cap 16 does not need to be sterile and can be reused. The reusable motor stator element 12 reduces the overall cost of the blood pump 10. The reusable motor stator element 12 reduces the overall cost of the blood pump by allowing the user to reuse the stator element numerous times, thereby reducing the overall per unit cost of the entire blood pump 10. In addition, the blood pump 10 according to the present invention greatly reduces the priming volume of the system when placed close to the patient thereby reducing the amount of saline and anti-coagulants which are introduced into the patient's blood. By placing the pump close to or within the surgical field the likelihood that a patient will require a blood transfusion is reduced. The pump according to the present invention can be used for either beating heart or still heart surgeries. As illustrated in FIGS. 1 and 2, the pump body 14 includes a blood inflow port 26 arranged axially with respect to the pump impeller 18 and a blood outflow port 28 arranged substantially tangent to an exterior of the pump body 14. The pump body 14 has a cylindrical side wall 30 extending from an impeller chamber 32 and configured to surround the reusable motor stator 12.

FIG. 2 illustrates an impeller 18 arranged in the impeller chamber 32 and non-rotatably connected to a cylindrical magnet 34 positioned within a magnet housing 44. The magnet housing 44 hermetically seals the impeller chamber 32 from the motor stator 12 and affords protection against the formation of emboli. Bearings 36, 38 rotatable support the cylindrical magnet 34 and impeller 18. The impeller 18 is to the cylindrical magnet 34 by a shaft 40 extending through a flexible blood seal 42. The blood seal 42 may be constructed of Teflon, silicone, or any other bio-compatible material which prevents blood from the impeller chamber 32 from passing into the magnet housing 44. The cylindrical magnet 34 and bearings 36, 38 are surrounded by and supported in the magnet housing 44 which has a generally cylindrical shape and is configured to be received within a central bore of the reusable motor stator element 12. The impeller 18 includes a plurality of vanes arranged to move the blood from the inflow port 26 to the outflow port 28. As is known in the art, the vanes preferably do not contact the walls of the impeller chamber 32.

The reusable motor stator element 12 is any one of the known motor elements having a cylindrical central bore 48 for receiving and driving a rotatable cylindrical magnet element such as the cylindrical magnet 34. One example of a suitable motor stator element 12 is available as motor # 22an100aa from Koford Engineering, Lisle, Ill.

The motor stator element 12, as shown in FIG. 1, includes two locating recesses 50, 52 in a top surface 54 thereof. The motor stator element 12 also includes a longitudinal groove 56 along a cylindrical side surface 58 of the element. The locating recesses 50, 52 and the longitudinal groove 56 function to allow the pump body 14 to be received over the motor stator element 12 in only one particular desired orientation.

The pump body 14, as shown in FIGS. 2 and 3, preferably includes two locating pins 60, 62 which correspond to the locating recesses 50, 52 in the motor stator element 12. The pump body 14 also includes an interior key element 64 which is configured to be received in the longitudinal groove 56 in the motor stator element 12. It should be understood that one or more of the locating features described above may be used with or without the other locating features.

FIG. 4 shows the locking cap 16 which is received over a bottom surface 66 of the motor stator element 12 and provides electrical connections to the motor stator. The locking cap 16 includes an electrical cable 70 connected to an electrical connector 72 of the cap. The cap 16 also includes a locking element 76 and an annular sealing member 78. The cap 16 snaps onto the pump body 14 when the locking element 76 which is preferably a flexible element snaps into a groove 80 in the interior surface of the pump body cylindrical side wall 30. The annular sealing member 78 of the cap 16 is received in a sealing groove 82 in the pump body 14. When assembled, the pump body 14 and cap 16 provide a secure fluid tight hermetic seal to prevent contamination from the non-sterile motor stator element 12 from escaping into the sterile environment in which the blood pump 10 has been placed.

When assembled, the motor stator chamber may be evacuated through a port 74 disposed on the cap 16. Once evacuated, the chamber surrounding the motor stator 12 may be left in a state of negative pressure or carbon dioxide may be introduced into the chamber to equalize the pressure. If the fluid tight seal provided by the magnet housing 44 fails the negative pressure or carbon dioxide in the motor stator chamber prevents air bubbles or emboli from entering the patients blood stream. In fact if any of the seals between the pump body 14 and the motor stator 12 fail because of high suction pressure or some other unforseen accident, air will not enter the patient's blood stream. Instead if there is a vacuum in the motor stator chamber, the motor stator chamber will fill with blood and the leak will stop. If the motor stator chamber is filled with carbon dioxide, blood will readily absorb the carbon dioxide without the danger of a emboli formation.

Although the invention has been illustrated with a two component housing formed by the pump body 14 and the cap 16, it should be understood that the sterile housing may be formed from two or more members. The cylindrical side walls 30 may be formed as a part of the pump body 14, as shown, or as a part of the cap 16. Alternatively, the sterile housing may be formed around the motor stator element 12 as a one piece molded element.

After use and before disposal of the blood pump 10, the removable motor stator element 12 may be removed for reuse. In order to remove the motor stator element 12, the locking cap 16 is removed from the pump body 14 and the motor stator element 12 slides out of the pump body. Although the motor stator element 12 is preferably reusable, the entire blood pump assembly may also be disposable.

Figure 5:
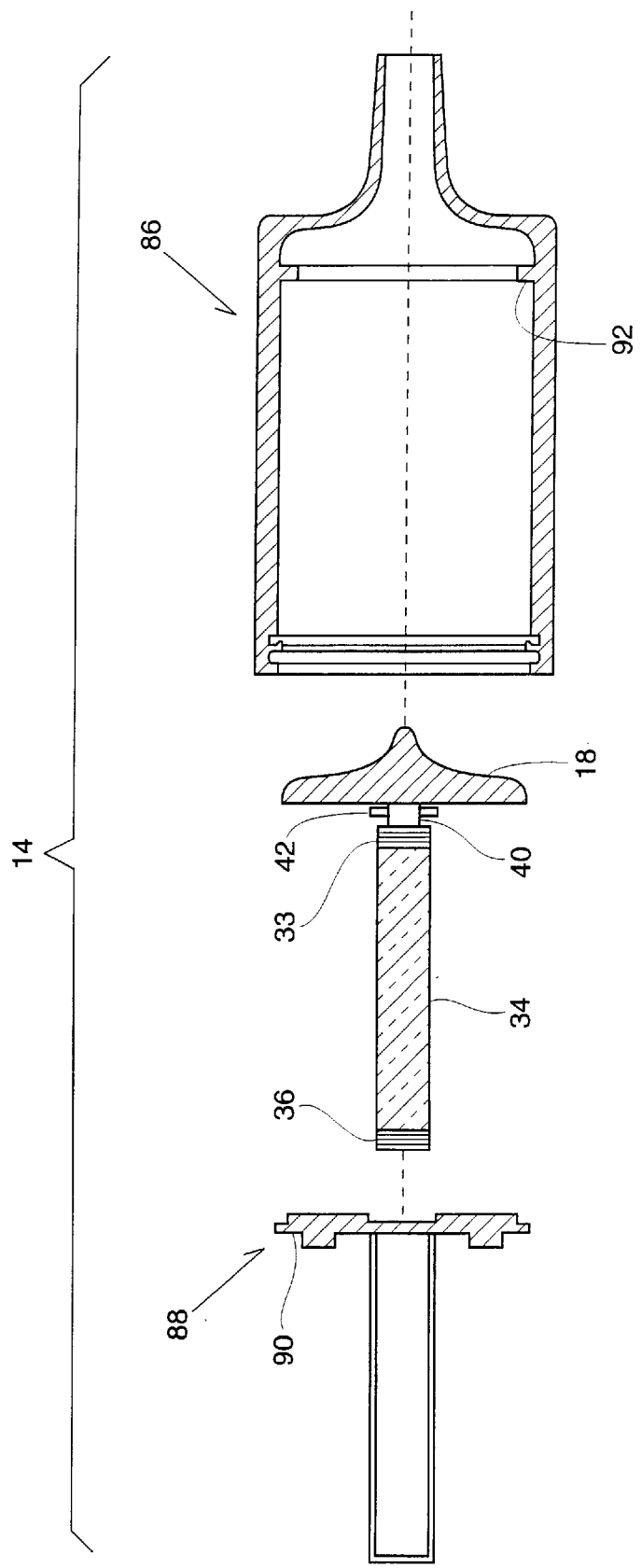
FIG. 5 is an exploded side cross sectional view of the pump element according to the present invention with the motor removed.

FIG. 5 illustrates one embodiment of a pump body 14 formed from two separate injection molded parts including a main body assembly 86 and a back plate assembly 88. The impeller 18 and cylindrical magnet 34 are assembled and inserted into the main body assembly 86. The back plate assembly 88 is then inserted into the main body assembly 86 until a flange 90 on the back plate assembly abuts a corresponding flange 92 on the main body assembly. The parts may be secured together with a bio-compatible glue, by ultrasonic welding, or any other known joining technique.

The locking cap 16 may be formed as a single injection molded piece. The electrical cable 70 and electrical connector 72 may be inserted into the locking cap 16 after molding and secured in place in a known fluid tight manner, such as with a bio-compatible glue. Alternatively, the electrical connector 72 may be secured within the locking cap 16 during the molding process. The electrical connector 72 is configured to be received in a corresponding electrical connector of the motor stator element 12 and provides power to the motor and feedback from the motor stator element to a control panel. In addition, the cable 70 may include a plurality of gas lines that can be used to cool the motor stator element. One of the gas lines may be used for delivery of carbon dioxide cooling gas and another of the gas lines would be connected to a vacuum to withdraw heated carbon dioxide.

Figure 6:
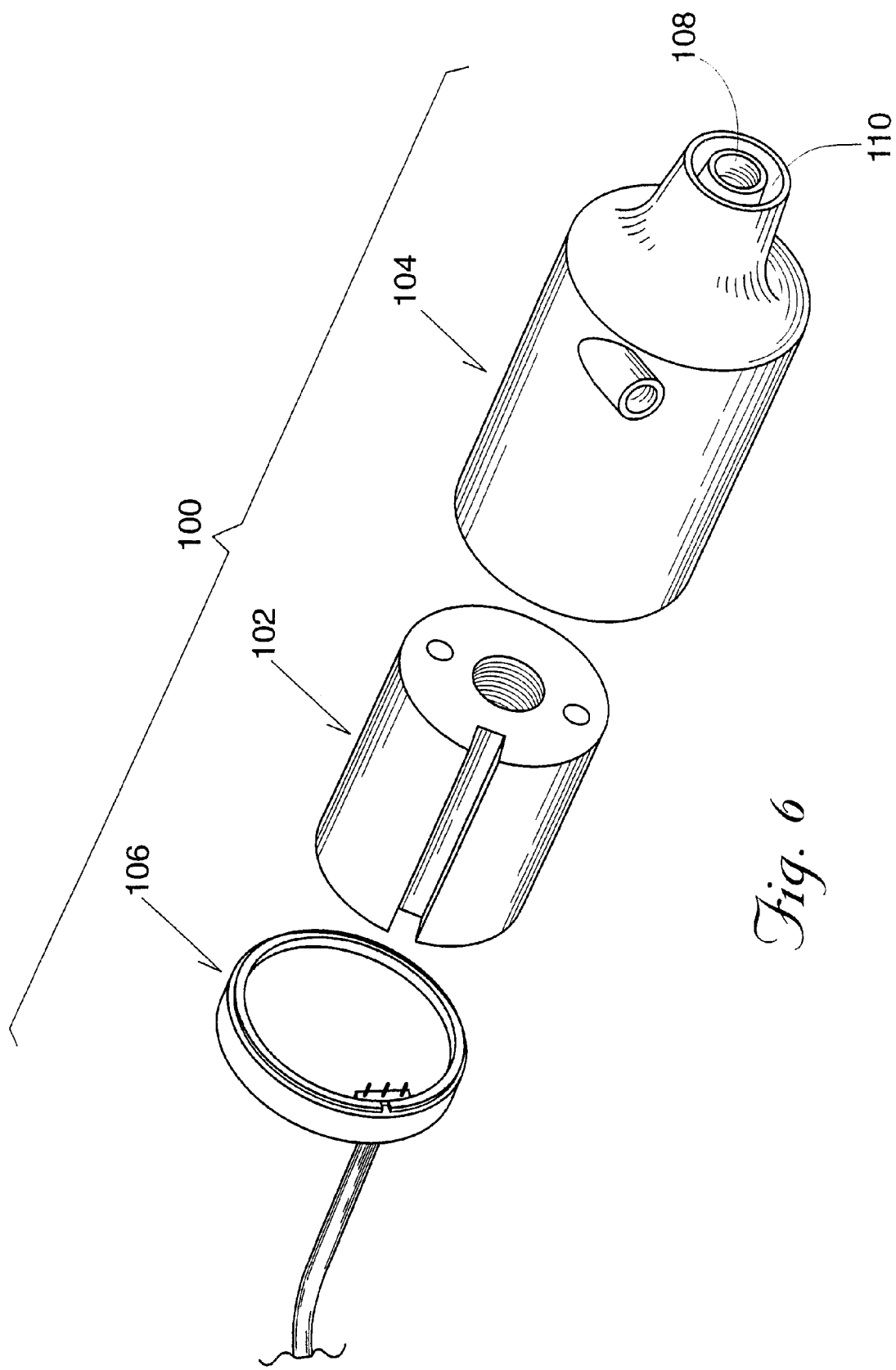
FIG. 6 is an exploded perspective view of a blood pump with a coaxial blood inlet and blood outlet.

FIG. 6 illustrates an alternative embodiment of a blood pump 100 including a reusable motor stator element 102, a pump body 104, and a cap 106. The pump body 104 includes an axial blood inlet 108 and a coaxial blood outlet 110 surrounding the blood inlet. According to this coaxial blood pump embodiment of FIG. 6, a single coaxial blood tube can be used to deliver blood to and from the patient. This configuration provides space savings and allows the blood tubing to enter the patient through a single incision.

FIG. 7 and 8 illustrate an alternative embodiment of the blood pump 10 of FIG. 1 in which a sterile sleeve 120 is connected to an end of the pump body 14. The sterile sleeve 120 is formed of a flexible material such as polypropylene, polyethylene, or the like, and may be connected to the pump body 14 before or after sterilization of the pump body. According to the embodiment of FIG. 7 and 8, the sterile sleeve 120 is initially folded or otherwise compressed longitudinally and secured to the end of the pump body 14. Once the motor stator element 12 has been inserted into the pump body 14 and the cap 16 has been attached to the pump body, the sterile sleeve 120 is drawn down over the cap and the electrical cable 70. The sterile sleeve 120 allows the use of a nonsterile cap 16 and electrical cable 17 and provides a sterile environment. Alternatively, the cap 16 may be eliminated entirely or permanently connected to the motor stator element 12. The integral cap and motor stator element will eliminate the need for the electrical coupling.

FIG. 9 illustrates an alternative embodiment of a blood pump 130 in which the motor stator element 132 is received within a pump body 134 and a magnetic coupling 136 connects an output shaft of the motor stator element with the impeller 138 of the pump body. The magnetic coupling 136 includes a first magnetic disk 140 connected to the output shaft of the motor stator element 132 and a second magnetic disk 142 secured to a shaft of the impeller 138. The pump body 134 is provide with a sealing partition 144 between the first and second magnetic disks 140, 142.

A further alternative embodiment of a blood pump 150 having a mechanical coupling between a motor stator element 152 and an impeller 154 of a pump body 156 is shown in FIG. 10. The mechanical coupling includes a square shaft 160 connected to the impeller 154 and a corresponding square socket 162 fixed to the output shaft of the motor stator element 152. It should be understood that the square shaft 160 and corresponding socket 162 may be replaced with any other known mechanical coupling system.

According to a further alternative aspect of the present invention, the blood pump according to the present invention may be utilized as an implanted cardiac assist pump by eliminating the electric cable 70 and providing an implantable rechargeable battery within the pump. Preferably, the pump contains a rechargeable battery which is arranged in the pump housing so that the battery is adjacent the patient's skin surface. The battery can then be recharged by placing an inductive charger over the battery on the exterior of the patient's skin.

The blood pumps 10, 100, 130, 150 according to the present invention each provide a compact, sterile blood pump which can be placed within the surgical field and even within the chest cavity during heart surgery. The blood pump 10 may be used during beating heart or still heart surgery and may by used for minimally invasive surgery where the heart is accessed through the ribs or for conventional open chest surgery.

While the invention has been described in detail with reference to the preferred embodiments thereof, it will be apparent to one skilled in the art that various changes and modifications can be made and equivalents employed, without departing from the present invention.

What is claimed is:

1. A blood pump, comprising:
    a motor stator element having a substantially cylindrical central cavity and an electrical connection;
    a disposable pump housing including an impeller chamber having a fluid inlet and a fluid outlet, a stator chamber for receiving said motor stator, a cap member for selectively sealing said stator within said stator chamber, and a rotor chamber for receiving a rotor element therein, said rotor chamber being received completely within said substantially cylindrical cavity of said motor stator and substantially sealed off from said stator chamber and said impeller chamber via at least one of a blood seal and a sealing partition; and
    a pump assembly having an impeller disposed within said impeller chamber, and a substantially cylindrical magnetic rotor disposed within said rotor chamber and coupled to said impeller;
    wherein said motor stator may be received within said stator chamber of said pump housing and the cap member thereerafter secured to completely enclose and isolate said motor stator element.

2. The blood pump of claim 1, wherein said fluid inlet of said impeller chamber is an axial fluid inlet and said fluid outlet of said impeller chamber is a tangential fluid outlet.

3. The blood pump of claim 1, wherein said fluid inlet of said impeller chamber is an axial fluid inlet and said fluid outlet of said impeller chamber is a coaxial fluid outlet.

4. A blood pump, comprising:
a motor stator element having a substantially cylindrical central cavity and an electrical connection;
a disposable pump housing including an impeller chamber having a fluid inlet and a fluid outlet, a stator chamber for receiving said motor stator, a cap member for selectively sealing said stator within said stator chamber, a rotor chamber for receiving a rotor element therein, and a seal disposed between said impeller chamber and said rotor chamber, said rotor chamber being received completely within said substantially cylindrical cavity of said motor stator and substantially sealed off from said stator chamber and said impeller chamber via said seal; and
a sterile pump assembly having an impeller disposed within said impeller chamber, a substantially cylindrical magnetic rotor disposed within said rotor chamber and coupled to said impeller, and a shaft extending between said rotor and said impeller;
wherein said motor stator may be received within said stator chamber of said pump housing said the cap member thereafter secured to completely enclose and isolate said motor stator element.

5. A blood pump, comprising:
a reusable motor stator element having a substantially cylindrical central cavity and an electrical connection;
a disposable pump element having an impeller coupled to a substantially cylindrical magnetic rotor which is configured to fit within the substantially cylindrical central cavity of the motor stator element; and
a cap member having a fluid tight connection for connecting the cap member to the pump element to completely enclose and isolate the motor stator element within a pump housing formed by the pump element and the cap member, wherein the pump element includes a first locating element and the motor stator element includes a second locating element which engages the first locating element to fix a relative position of the pump element and the motor stator element.

6. The blood pump of claim 5, wherein the first locating element is a key member and the second locating member is a slot positioned on a side wall of the motor stator for receiving the key element.

7. The blood pump of claim 5, wherein the pump housing includes an electrical connection for connecting to the electrical connection of the motor stator element to power the motor stator element and the locating elements ensure the particular orientation of the pump housing and the motor stator to allow the electrical connection to be made.

8. A blood pump, comprising:
a motor stator element having a substantially cylindrical central cavity and an electrical connection;
a disposable pump housing including an impeller chamber having a fluid inlet and a fluid outlet, a stator chamber for receiving said motor stator, a cap member for selectively sealing said stator within said stator chamber, a rotor chamber for receiving a rotor element therein, and a flexible sterile sleeve extending from the disposable pump housing over the cap member, wherein said rotor chamber is dimensioned to be received within said substantially cylindrical cavity of said motor stator and is substantially sealed off from said stator chamber and said impeller chamber; and
a pump assembly having an impeller disposed within said impeller chamber, and a substantially cylindrical magnetic rotor disposed within said rotor chamber and coupled to said impeller;
wherein said motor stator may be received within said stator chamber of said pump housing and the cap member thereafter secured to completely enclose and isolate said motor stator element.

9. A blood pump assembly, comprising:
a disposable blood pump having an impeller chamber with a rotatable impeller disposed therein for moving blood from a blood inlet to a blood outlet, a rotor chamber with a rotatable rotor disposed therein which is coupled to said impeller, a stator chamber dimensioned to completely receive said rotor chamber, and a cap member for selectively opening and closing said stator chamber, said rotor chamber being substantially sealed from said impeller chamber via at least one of a blood seal and a sealing partition; and
a motor stator element configured to be received within the stator chamber of said disposable blood pump, said motor stator element having a generally cylindrical receiving area formed therein configured to receive said rotor chamber of said blood pump when said motor stator element is introduced into and sealed within said stator chamber, wherein the motor stator element is thereby capable of magnetically driving said rotor and said impeller of said blood pump.

10. A blood pump assembly, comprising:
a disposable blood pump having an impeller chamber with a rotatable impeller disposed therein for moving blood from a blood inlet to a blood outlet, a rotor chamber with a rotatable rotor disposed therein which is coupled to said impeller, a stator chamber disposed generally cylindrically about said rotor chamber, a cap member for selectively opening and closing said stator chamber, and an electrical cable coupled to an electrical connection on said cap member, said rotor chamber being substantially sealed from said impeller chamber and from said stator chamber; and
a motor stator element configured to be received within the stator chamber of said disposable blood pump, said motor stator element having a generally cylindrical receiving area formed therein configured to reactive said rotor chamber of said blood pump when said motor stator element is introduced into and sealed within said stator chamber, wherein said electrical connection on said cap member is configured to electrically connect said electrical cable to an electrical connection of said motor stator element to magnetically drive said rotor and said impeller of said blood pump.

11. A blood pump assembly, comprising:
a disposable blood pump having an impeller chamber with a rotatable impeller disposed therein for moving blood from a blood inlet to a blood outlet, a rotor chamber with a rotatable rotor disposed therein which is coupled to said impeller via a shaft member, a seal member disposed between said impeller chamber and said rotor member having an aperture for allowing said shaft member to pass therethough while substantially sealing said impeller chamber from said rotor chamber, a stator chamber disposed generally cylindrically about said rotor chamber, and a cap member for selectively opening and closing said stator chamber; and
a motor stator element configured to be received within the stator chamber of said disposable blood pump, said motor stator element having a generally cylindrical receiving area formed therein configured to receive said rotor chamber of said blood pump when said motor stator element is introduced into and sealed within said stator chamber, wherein the motor stator element is thereby capable of magnetically driving said rotor and said impeller of said blood pump.

12. A sterile blood pump assembly, comprising:
   a blood pump having a blood inlet, a blood outlet, and an impeller for pumping blood from the inlet to the outlet, the impeller coupled to a magnetic rotor element;
   a motor stator element configured to be received in the blood pump with the magnetic rotor element of the blood pump received within a coil winding of the motor stator element, wherein the motor stator element rotates the magnetic rotor element and the impeller of the blood pump element; and
   a sterile housing surrounding the motor stator element and isolating the motor stator element from a surrounding environment, wherein the blood pump element includes a first locating element and the motor stator element includes a second locating element which engages the first locating element to fix a relative position of the blood pump element and the motor stator element.

13. The sterile blood pump assembly of claim 12, wherein the first locating element is a key member and the second locating member is a slot positioned on a side wall of the motor stator for receiving the key element.

14. The sterile blood pump assembly of claim 13, wherein the first locating element is a locating pin and the second locating element is a recess for receiving the locating pin in a particular orientation.

15. The sterile blood pump assembly of claim 12, wherein the sterile housing is evacuated to form a vacuum around the motor stator element such that if a seal in the blood pump element fails, fluid will be drawn into the sterile housing eliminating the possibility of the formation of emboli within the patient's blood stream.

16. A method of pumping blood during heart surgery, the method comprising:
   providing a sterile pump housing including an impeller chamber, a rotor chamber, a stator chamber, and a cap member;
   providing a sterile pump assembly within said sterile pump housing, said sterile pump assembly including an impeller disposed within said impeller chamber, and a magnetic rotor disposed within said rotor chamber and coupled to said impeller;
   isolating a motor stator within said sterile pump housing by disposing said motor stator within said stator chamber and securing said cap member, said motor stator being completely sealed from said rotor chamber and said impeller chamber;
   placing the sterile pump housing within a sterile surgical field; and
   activating said motor stator to magnetically drive said rotor and said impeller and thereby pump a patient's blood by rotation of said impeller.

17. The method of pumping blood during heart surgery of claim 16, further comprising the steps of removing said motor stator from said sterile pump housing, disposing said sterile pump housing, and reusing said motor stator.

18. The method of pumping blood during heart surgery of claim 16, wherein said sterile pump housing used to isolate said motor stator includes a flexible sleeve extending from the sterile pump housing.

19. The method of pumping blood during heart surgery of claim 16, wherein the sterile pump housing used to isolate the motor element includes a cylindrical side wall and a cap for forming a fluid tight seal with the cylindrical side wall.

20. A blood pump, comprising:
   a motor assembly including a reusable stator element and a sterile rotor assembly, the reusable stator element having a generally cylindrical central cavity, an electrical connector, and a registration mechanism, the sterile rotor assembly including a generally cylindrical rotor rotatably coupled to an impeller; and
   a sterile housing including a pump body and a cap member, the pump body defining an impeller chamber, a stator chamber, and a rotor chamber, the impeller chamber having a blood inlet and blood outlet, the stator chamber having a registration mechanism for engaging with the registration mechanism of the stator element to automatically register the stator element in a predetermined orientation when positioned within the stator chamber.

* * * * *